United States Patent
Kohno

Patent Number: 5,528,360
Date of Patent: Jun. 18, 1996

[54] SURFACE-CONDITION INSPECTION APPARATUS

[75] Inventor: Michio Kohno, Tokyo, Japan

[73] Assignee: Canon Kabushiki Kaisha, Tokyo, Japan

[21] Appl. No.: 479,357

[22] Filed: Jun. 7, 1995

Related U.S. Application Data

[63] Continuation of Ser. No. 945,412, Sep. 15, 1992, abandoned.

[30] Foreign Application Priority Data

Sep. 20, 1991 [JP] Japan .................. 3-241395

[51] Int. Cl.⁶ ........................... G01N 21/88
[52] U.S. Cl. ........................... 356/237; 356/431
[58] Field of Search ............... 356/390, 394, 356/398, 237, 429, 431

[56] References Cited

U.S. PATENT DOCUMENTS

| | | | |
|---|---|---|---|
| 3,909,602 | 9/1975 | Micka | 356/398 |
| 3,944,369 | 3/1976 | Cuthbert et al. | 356/398 |
| 4,013,367 | 3/1977 | Nagao et al. | 356/431 |
| 4,595,289 | 6/1986 | Feldman et al. | 356/237 |
| 4,681,453 | 7/1987 | Sick | 356/398 |
| 4,795,911 | 1/1989 | Kohno et al. | 250/572 |
| 4,831,274 | 5/1989 | Kohno et al. | 250/563 |
| 4,871,257 | 10/1989 | Suzuki et al. | 356/400 |
| 5,017,798 | 5/1991 | Murakami et al. | 386/431 |
| 5,105,092 | 4/1992 | Natsubori et al. | 250/572 |

Primary Examiner—Richard A. Rosenberger
Attorney, Agent, or Firm—Fitzpatrick, Cella, Harper & Scinto

[57] ABSTRACT

Beam scanning accompanying the rotation of a polygonal mirror for scanning is performed while projecting two light beams having different incident angles onto the polygonal mirror, and simultaneously illuminating positions having the same shape on patterns having the same shape on a reticle by two light beams reflected by the polygonal mirror. Light beams from the respective irradiated points are separately detected and compared with each other, whereby the presence of a foreign particle or the like is inspected. The interval between the irradiated points is changed by the function of an actuator in order to deal with changes and errors in the distance between patterns on different reticles.

10 Claims, 15 Drawing Sheets

SURFACE-CONDITION INSPECTION APPARATUS

This application is a continuation of prior application, Ser. No. 07/945,412 filed Sep. 15, 1992, now abandoned.

BACKGROUND OF THE INVENTION

1. Field of the Invention

This invention relates to a surface-condition inspection apparatus, and more particularly, to a surface-condition inspection apparatus which is suitable for detecting pattern defects or foreign particles, such as dust particles or the like, present on a substrate, such as a reticle, a photomask or the like, used in the production of semiconductor devices.

2. Description of the Prior Art

In general, in the IC (integrated circuit) production process, circuit patterns to be exposed are formed on a substrate, such as a reticle, a photomask or the like, and are transferred onto the surface of a wafer coated with a resist using a semiconductor printing apparatus (a stepper or a mask aligner).

If foreign particles, such as dust particles or the like, are present on the surface of the substrate at the time of circuit pattern transfer, the foreign particles are also transferred, causing a decrease in the yield of the IC production.

In particular, when circuit patterns are printed onto the surface of a wafer by the step-and-repeat method using a reticle, one foreign particle present on the surface of the reticle is printed onto the entire surface of the wafer, causing a great decrease in the yield of the IC production. Accordingly, the ability to detect the presence of a foreign particle on a substrate in the IC production process is indispensable, and various kinds of inspection apparatuses have been proposed for that purpose.

FIG. 15 shows an example of such a conventional apparatus. This apparatus has a feature in that one light beam is simultaneously projected onto two surfaces to be inspected (a pattern surface and a blank surface) of a reticle, whereby time for inspection is shortened. That is, an incident light beam 3 passing through an f-8 lens 2, serving as a lens for projecting light, is divided into two light beams by a half-mirror 4. The resulting two light beams are focused onto points P and Q on the respective surfaces of the reticle 1 by reflecting mirrors 5 and 10 provided above and below the reticle 1, respectively. Usually, the surface of the reticle having circuit patterns (the pattern surface) faces downward, and the other surface which is blank (the blank surface) faces upward. When inspecting for circuit defects, only the pattern surface needs to be inspected. However, when inspecting foreign particles, both the pattern surface and the blank surface must be inspected. A rotating element (a polygonal mirror, not shown) is provided in front of the projection lens 2, and performs scanning of the light beam in a direction orthogonal to the plane of FIG. 15. The upper and lower light beams thereby scan the surfaces of the reticle 1 in the direction orthogonal to the plane of FIG. 15. The reticle 1 is moved in the direction $S_1 \leftarrow S_2$ in synchronization with the scanning of the light beams, whereby the entire surfaces of the reticle 1 are inspected. Thus, the pattern surface and the blank surface of the reticle 1 are subjected to two-dimensional scanning (raster scanning). Scattered light reflected from the incident point P on the reticle 1 is imaged onto a field stop 7a by the function of a light-receiving lens 6a. The field stop 7a has the function of guiding only necessary signal light to a fiber 8a and a photomultiplier 9a which follow, and shielding other unnecessary light. According to the above-described configuration, an upper light-receiving system 30 is formed, which enables inspection for the presence of foreign particles or the like using the output of the photomultiplier 9a. A light-receiving system 31 for scattered light emanating from the incident point Q has the same configuration (a light-receiving lens 6b, a field stop 7b, a fiber 8b and a photomultiplier 9b) as the above-described configuration.

Reticle patterns to be inspected can be arranged in various ways. For example, patterns for two chips can be provided on one reticle (two-chip arrangement) as shown in FIGS. 16(a) and 16(c), or a pattern for one chip can be provided on one reticle (one-chip arrangement) as shown in FIG. 16(b). Each of A, B, C, F and G in FIGS. 16(a)–16(c) represents a transfer-pattern forming portion for one chip. In the case of the two-chip arrangement, chips having the same patterns are in many cases repeated in order to increase the production yield. Respective chips are isolated by a non-pattern region LS, having a width equal to or less than 1 mm, called a scribing line.

The conventional inspection method by laser-beam scanning as shown in FIG. 15 is based on a principle in which basically, each surface to be inspected is scanned with one light beam irrespective of chip arrangement (one-chip arrangement or a plural-chip arrangement) on a reticle, and if a foreign particle is present, only light scattered by the foreign particle is detected by spatially separating as much as possible the scattered light from the light diffracted by a circuit pattern.

FIG. 17 shows a second example of the prior art, which is an apparatus for comparatively inspecting a plurality of chips arranged on a wafer. In FIG. 17, there are shown illuminating systems 20. Objective lenses 22 image respective chip patterns onto position sensors 23. A plurality of chips having the same pattern are repeatedly formed on the wafer. The optical axes of the objective lenses 22 are set onto the same patterns within two of the plurality of chips. The principle of the apparatus resides in comparing respective picture elements of the two position sensors 23 by a comparator 24, which outputs a signal only if an abnormality (a defect or a foreign particle) is present in any of the chips.

Although the first conventional apparatus (shown in FIG. 15) has the advantage that inspection time is short because of laser-beam scanning, the apparatus is required to have an ability to detect a foreign particle or the like with higher precision due to both a reduction in the size of a particle to be inspected in accordance with finer circuit patterns and an increase in pattern noise caused thereby.

Although the second conventional apparatus (shown in FIG. 17) has a high ability to detect a particle, which may be further increased by increasing the magnification of the objective lens, the apparatus has a narrow field of view which will be further reduced by increasing the magnification of the objective lens. Hence, in order to inspect the entire range to be inspected, the size of the detection unit must be increased by increasing the number of picture elements, or the mask must be frequently moved. A larger detection unit will result in a larger apparatus. On the other hand, when the mask must be moved frequently, the entire inspection time is longer than that of the laser-beam scanning method by one order of magnitude. For example, while it requires less than ten minutes to inspect a mask having a size of 100 mm square by the laser-beam scanning method, it requires more than 100 minutes to inspect the same mask by the image comparison method.

SUMMARY OF THE INVENTION

The present invention has been made in consideration of the above-described problems in the prior art.

It is an object of the present invention to provide a surface-condition inspection apparatus which performs inspection with high precision while maintaining a high-speed inspection capability and small size.

It is another object of the present invention to provide a small-sized surface-condition inspection apparatus which can perform inspection with high speed and high precision irrespective of a state of arrangement of a plurality of chip patterns on a reticle.

These and other objects are accomplished, according to one aspect of the present invention, by an apparatus for inspecting a surface condition of an object to be inspected. The apparatus includes beam scanning means for forming a plurality of scanning beams for scanning different portions on the object. An adjustment means adjusts an arrangement of the scanning beams to align each of the plurality of scanning beams relative to respective different portions on the object, and light detection means detects light beams from respective different portions on the object scanned by the respective scanning beams. An inspection means inspects a surface condition of the object utilizing detection signals corresponding to the respective scanning beams obtained from the light detection means.

According to another aspect, the present invention relates to an exposure apparatus for exposing and transferring patterns on an original onto an object to be exposed. The apparatus includes beam scanning means for forming a plurality of scanning beams for scanning different portions on the original. An adjustment means adjusts an arrangement of the plurality of scanning beams to align each of the plurality of scanning beams relative to respective different portions on the original, and a light detection means detects respective light beams from respective different portions on the original scanned by the respective scanning beam. An inspection means inspects a surface condition of the original utilizing detection signals corresponding to the respective scanning beams obtained from the light detection means.

According to yet another aspect of the present invention, an exposure method is provided for processing a semiconductor wafer in a semiconductor-device production process. The method includes forming first and second beams for projecting onto an original and projecting onto an original and projecting the first and second beams onto respective portions of the original. Scanning of the first and second portions of the original is performed with the first and second beams by deflecting the first and second beams. Independent detection is made of first and second radiations received from respective portions of the original in response to the projecting step. A condition of the original is then inspected by using a difference between the detected magnitudes of the first and second radiations. The semiconductor wafer is then exposed through the original.

According to still a further aspect of the present invention, an inspection method is provided which includes forming first and second beams for projection onto an object and projecting the first and second beams onto respective portions of the object. Scanning of the first and second portions of the object is performed with the first and second beams by deflecting the first and second beams. Independent detection is made of first and second radiations received from respective portions of the object in response to the projecting step. A condition of the object is then inspected by using a difference between the detected magnitudes of the first and second radiations.

DESCRIPTION OF THE PREFERRED EMBODIMENTS

Figure 1:
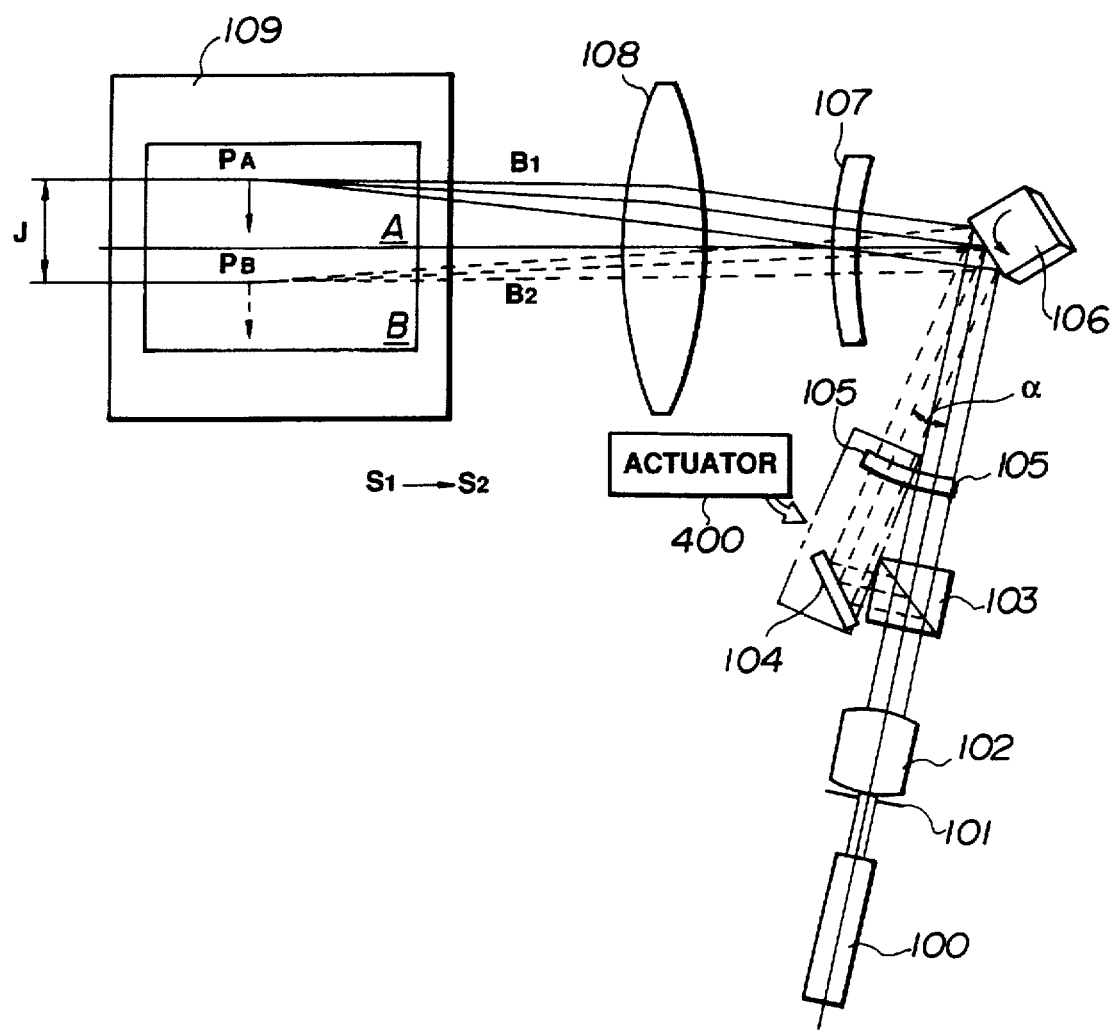
FIG. 1 is a top plan view showing the schematic configuration of a first embodiment of the present invention.

FIG. 1 is a top plan view showing the schematic configuration of a first embodiment of the present invention. In FIG. 1, a light beam emitted from a laser 100 is expanded to a predetermined light beam after passing through a pinhole 101 and a beam expander 102, and is incident upon a prism 103, where the light beam is divided into a directly-advancing light beam $B_1$, and a light beam $B_2$ reflected by a beam splitter provided within the prism 103 and further reflected by a mirror 104. The respective light beams are incident upon a cylindrical lens 105. The two light beams then advance toward a polygonal mirror 106 with a separation angle $\alpha$ (deg.). After being reflected by the polygonal mirror 106, the respective beams pass through a toric lens 107 (the functions of the lenses 105 and 107 will be explained below). The light beams $B_1$ and $B_2$ pass through a scanning lens 108, and form focused light beams at points $P_A$ and $P_B$, respectively, on a reticle 109. The points $P_A$ and $P_B$ are separated by an inter-chip pitch J. The respective focused light beams linearly scan the surface of the reticle 109 from top to bottom on the plane of FIG. 1 in accordance with the rotation of the polygonal mirror 106. The reticle 109 is moved in a direction (direction $S_1 \rightarrow S_2$ in FIG. 1) orthogonal to the direction of the beam scanning in synchronization with the beam scanning. As a result, regions A and B on the reticle 109 are inspected two-dimensionally by the light beams $B_1$ and $B_2$, respectively.

Chip patterns for transfer having the same shape are formed on the regions A and B in order to simultaneously produce the same chips. The scanning lens 108 comprises an ideal f-θ lens, and the interval J between the irradiated points $P_A$ and $P_B$ is always constant during the scanning provided that the optical systems of the respective light beams are fixed.

Figure 2:
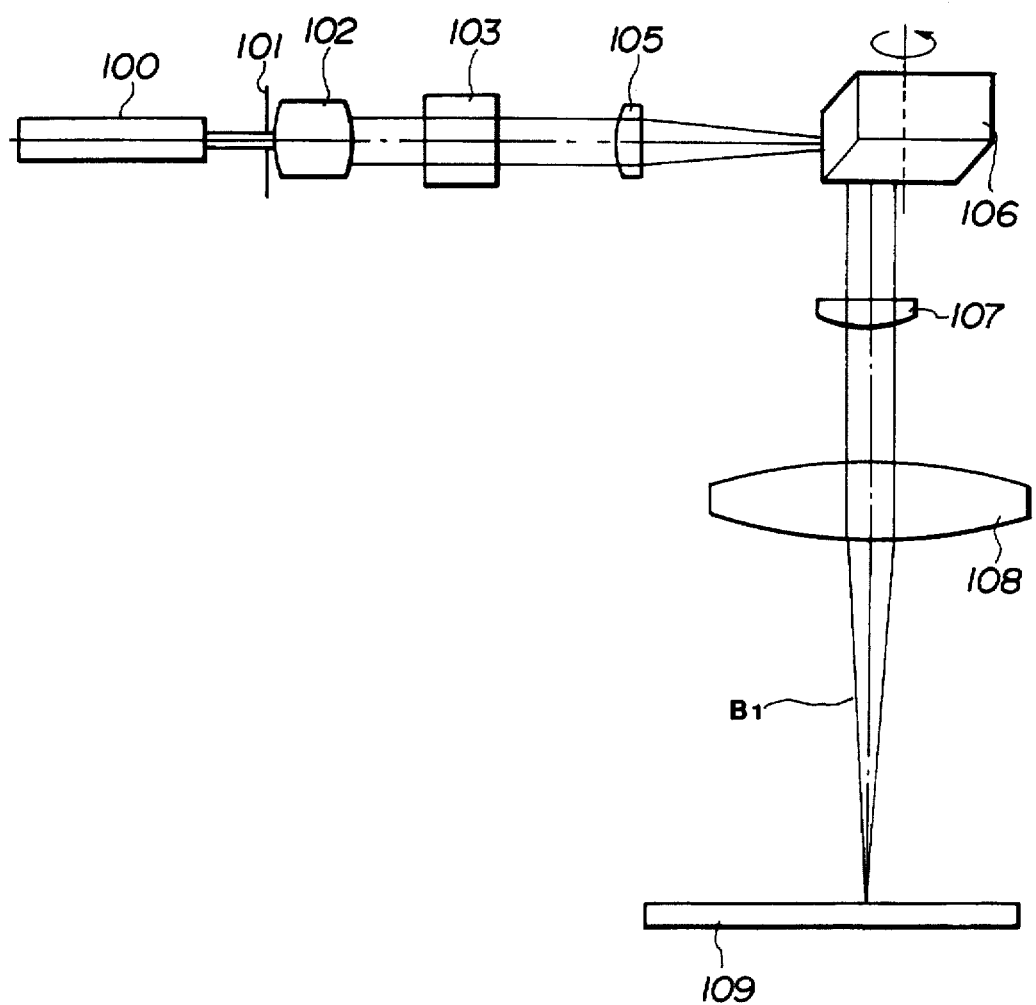
FIG. 2 is a side view showing the schematic configuration of the first embodiment.
Figure 3:
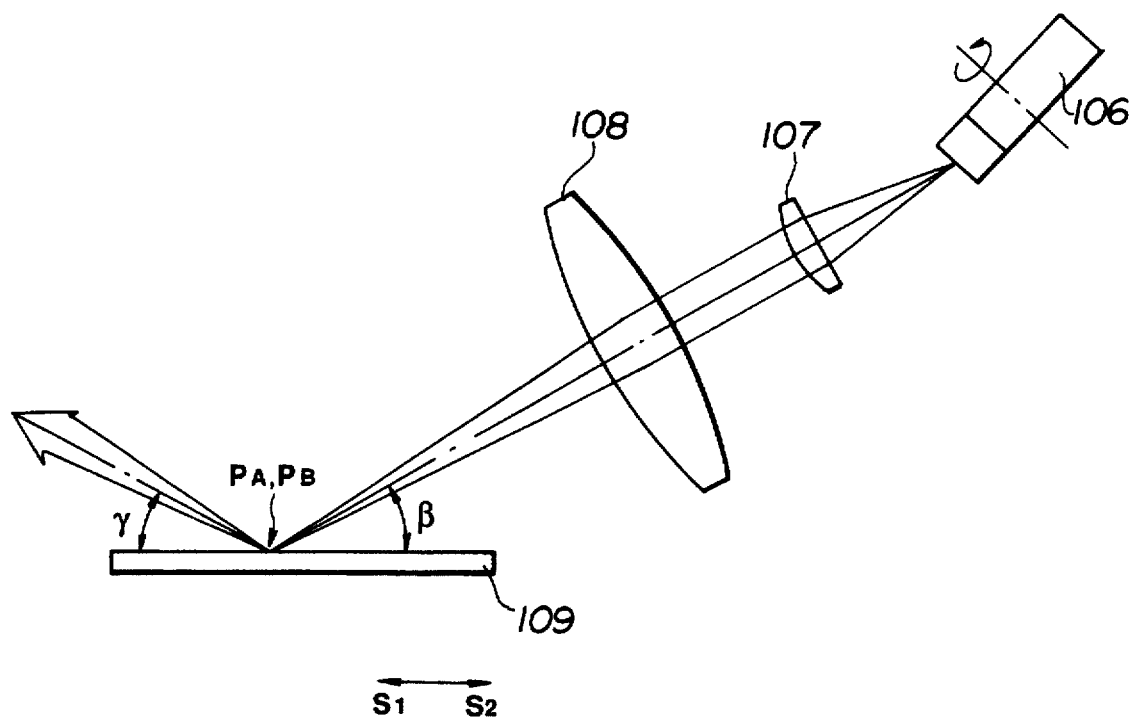
FIG. 3 is a front view showing the schematic configuration of the first embodiment.

FIG. 2 is a side view of the apparatus shown in FIG. 1 viewed from the right side. FIG. 3 is a front view of the apparatus shown in FIG. 1. In FIGS. 2 and 3, the light beam $B_2$ is omitted. In FIG. 3, the portion of the optical system before the polygonal mirror 106 is omitted.

The above-described cylindrical lens 105 has the function of focusing the light beam onto the reflecting surface of the polygonal mirror 106 within the plane of FIG. 2. As shown in FIG. 3, the light beams reflected by the polygonal mirror 106 are incident upon the toric lens 107 as diffused light beams. The diffused light beams are made substantially parallel by the function of the toric lens 107. The substantially parallel light beams are incident upon the scanning lens 108, which forms focused light beams at points $P_A$ and $P_B$ on the reticle 109.

By thus arranging the reflecting surface of the polygonal mirror and the surface of the reticle in an image-forming relationship, stable scanning beams having no deviation of scanning lines on the reticle are obtained even if an inclination is present in the shaft or the reflecting surface of the polygon. The incident light beams are incident with an angle β (deg.) with respect to the reticle.

Figure 4:
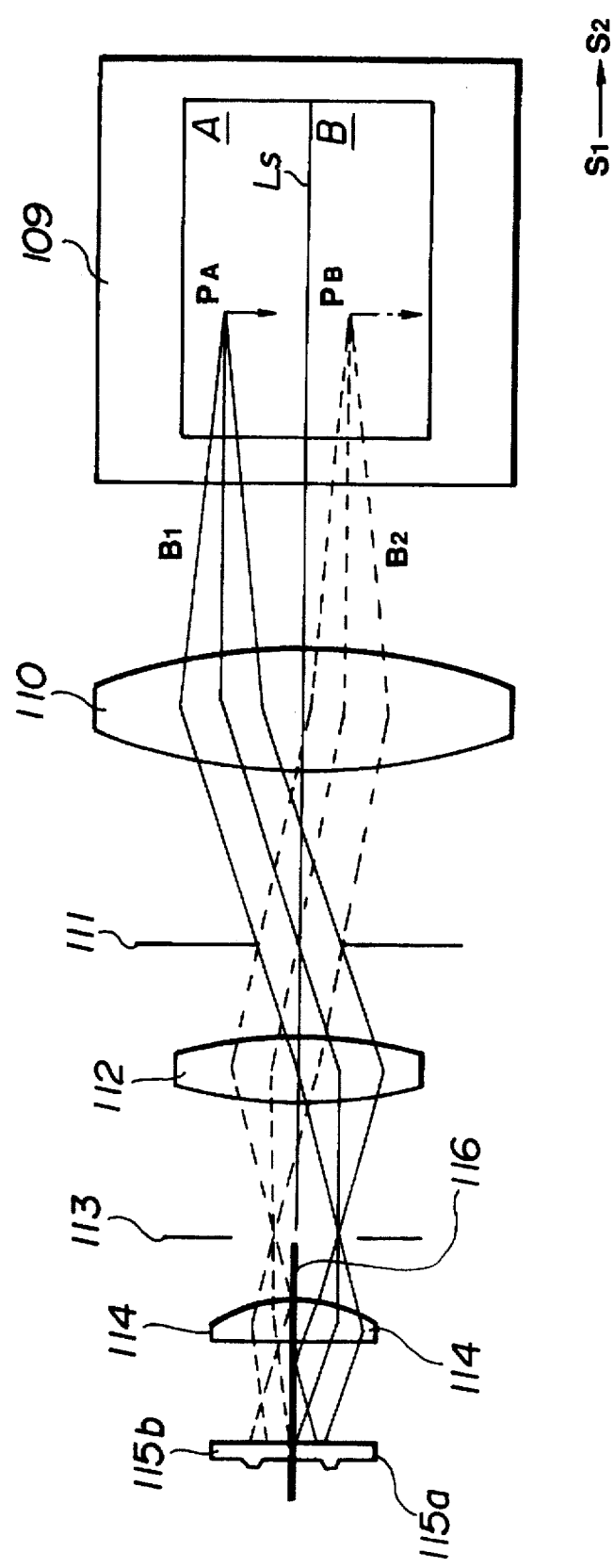
FIG. 4 is a top plan view showing the schematic configuration of a light-receiving optical system of the first embodiment.
Figure 5:
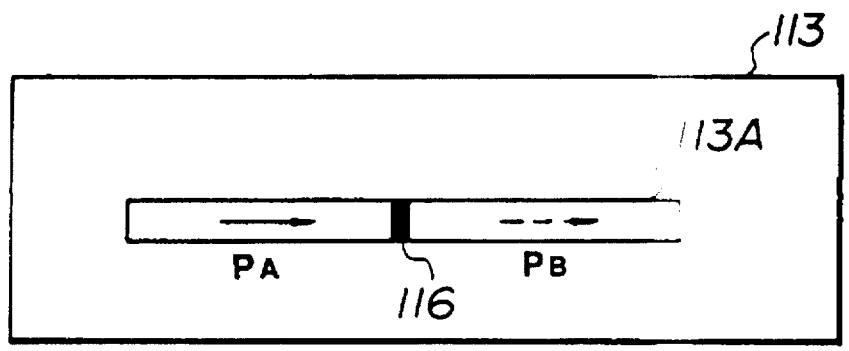
FIG. 5 is a diagram illustrating a field stop.
Figure 8:
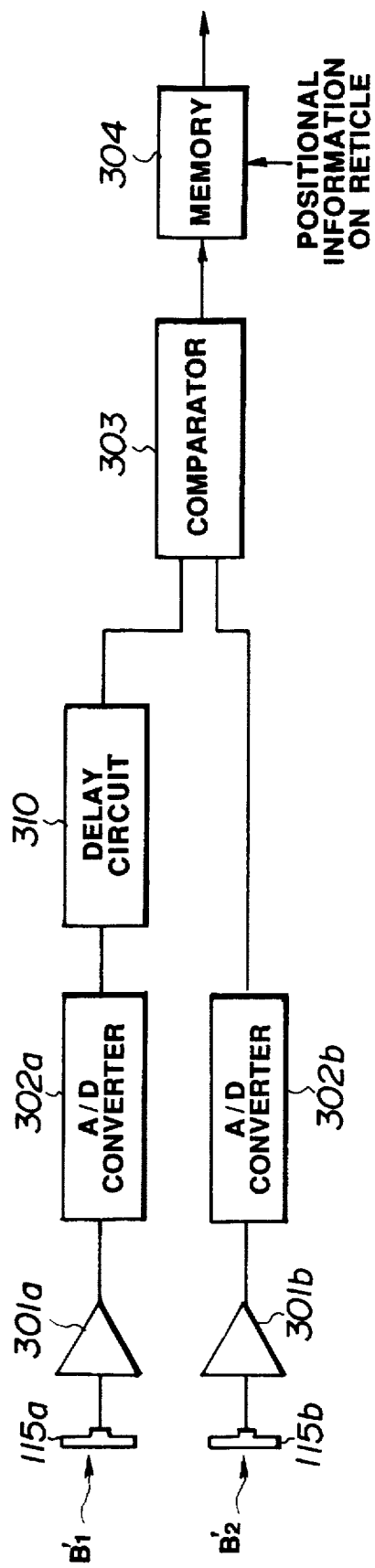
FIG. 8 is a diagram showing the schematic configuration of an alternative configuration of the electrical processing system.

An angle α (deg.) shown in FIG. 3 represents an angle of the optical axis of the light-receiving system with respect to the reticle. FIG. 4 is a diagram showing the schematic configuration of a light-receiving system of the apparatus of the first preferred embodiment. Reflected (or scattered) light beams from the respective points $P_A$ and $P_B$ on the reticle pass through a condensor lens 110 and an aperture stop 111 for limiting light beams, and are reimaged onto a field stop 113 by the function of an imaging lens 112. As shown in FIG. 8, the field stop 113 includes a slit aperture 113A having the shape of a rectangle whose longer side is in the beam scanning direction. The central portion of the slit aperture 113A is shielded by an end portion of a separation mirror 116, whereby the slit aperture 113A is divided into right and left portions as shown in FIG. 5. The separation mirror 116 separates the optical path toward detectors 115a and 115b into upper and lower portions as shown in FIG. 4. By thus configuring the system, unnecessary scattered light from the adjacent region on the reticle is shielded.

Respective light beams whose optical paths after the field stop 113 are separated by the separation mirror 116, which is disposed on the light-receiving optical axis, are made to be parallel or focused light beams by the function of divided lenses 114, and are guided to photoelectric transducers 115a and 115b, such as photomultipliers or the like.

Thus, by the function of the separation mirror 116, a light beam reflected from an arbitrary point on the chip region A on the reticle passes through the lower-half portion of the field stop 113 in FIG. 4 while being partly reflected by the separation mirror 116, and is guided to the detector 115a without a loss in the amount of light. In the same manner, a light beam reflected from an arbitrary point on the chip region B is guided to the detector 115b.

Figures 6A, 6B, 6C:
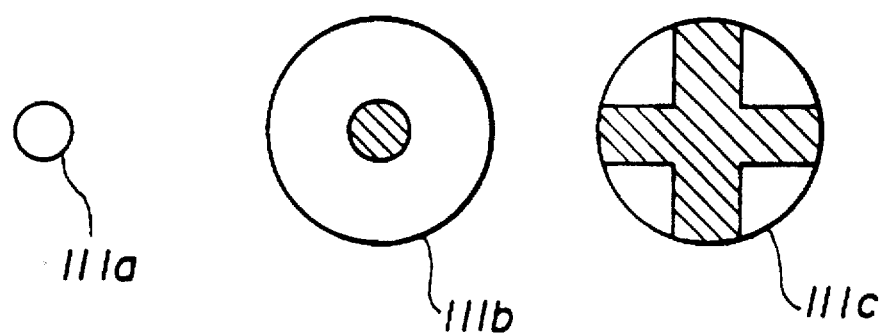
FIGS. 6(a) through 6(c) are diagrams illustrating aperture stops.

The above-described light beam to be received may be a O-order reflected light beam or a scattered light beam in an arbitrary direction from the reticle pattern. Referring again to FIG. 3, if the angle α of the light-receiving system is arranged to be equal to the angle β, the O-order reflected light beam becomes the light beam to be received. In other cases, a scattered light beam becomes the light beam to be received. FIGS. 6(a) through 6(c) show different shapes of the stop provided in the aperture stop 111.

If it is desired to receive the O-order light beam in the condition of β=α, a circular aperture as indicated by reference numeral 111a is selected. If it is desired to shield the O-order light beam and compare scattered light beams or light beams diffracted by the pattern in the vicinity of the O-order light beam, an aperture whose central portion is shielded, as indicated by reference numeral 111b, is selected. Alternatively, the stop 111a may be used while making β≠α. If it is desired to receive and compare light beams scattered by a foreign particle, while reducing as much as possible light beams diffracted by the circuit pattern, a spatial filter as indicated by reference numeral 111c may be used so that light beams diffracted by the pattern in the vertical and horizontal directions may be shielded.

Figure 7:
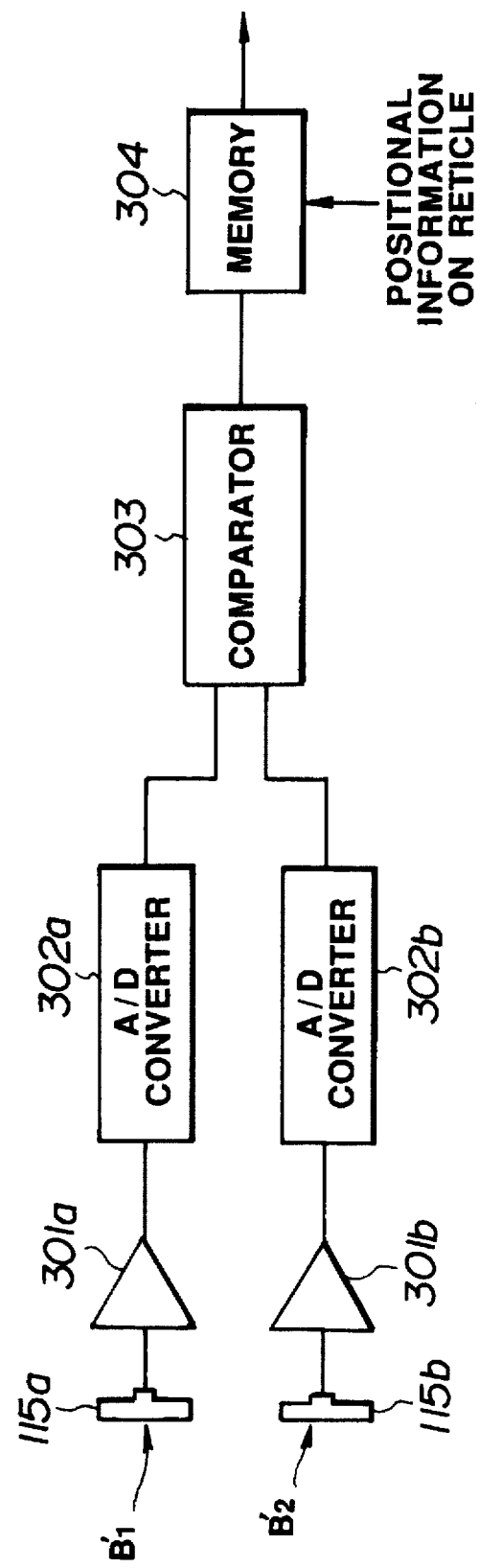
FIG. 7 is a diagram showing the schematic configuration of an electrical processing system of the first embodiment.

FIG. 7 is a diagram showing the schematic configuration of an electrical processing system for comparing and determining two photoelectric outputs. Patterns in the regions A and B have the same shape. Hence, if the patterns are equally scanned by the light beams $B_1$ and $B_2$, the outputs of the detectors 115a and 115b are equal if a foreign particle or the like is absent. Accordingly, detection signals representing the light beams $B'_1$ and $B'_2$ reaching the detectors 115a and 115b are amplified by amplifiers 301a and 301b, are then converted from analog signals into digital signals, and are input to a comparator 303. If the difference between the two outputs becomes at least a predetermined value, it is determined that a foreign particle is present, and the difference level and positional information regarding the particle's location on the reticle are stored in a memory 304 and will be output later. The positional information can be obtained from the timing of the beam scanning and the movement of the reticle.

Referring again to FIG. 1, if it is intended to determine the presence of a foreign particle or the like by the above-described comparison between the detection outputs, the light beams $B_1$ and $B_2$ must illuminate positions having the same shape on the respective chips while scanning the regions A and B, respectively. However, pattern arrangement on a reticle to be inspected is supposed to differ for each reticle. Accordingly, in the present apparatus, for the purpose of changing the incident angle of one of two light beams incident upon the polygonal mirror 106 (the light beam $B_2$ in the present embodiment), the mirror 104 and the cylindrical lens 105 are arranged to be rotatably driven as one body by an actuator 400. They are driven substantially around the point of reflection of the beams on the polygonal mirror 106. It is assumed that the points $P_A$ and $P_B$ irradiated by the respective light beams on the reticle 109 are adjusted to be at equal positions in the moving direction of the reticle ($S_1 \rightarrow S_2$). Suppose, for example, a case in which an error is present in the interval between the light beams on the regions A and B on the reticle in the beam-scanning direction for each reticle, or the designed interval originally differs. In such a case, by adjusting the interval J between the points $P_A$ and $P_B$ irradiated by the respective light beams on the reticle by changing the incident angle of the light beam $B_2$ on the polygonal mirror using the actuator 400, the light beams $B_1$ and $B_2$ can scan the regions A and B, respectively, while always simultaneously illuminating positions having the same shape on the respective patterns on the regions A and B. That is, if there is a difference in the interval between the regions A and B between the next reticle to be inspected and the preceding reticle, the operator adjusts the interval J between the points $P_A$ and $P_B$ irradiated by the respective light beams using the actuator 400 in accordance with the interval between the regions A and B on the next reticle to be inspected. Thus, positions having the same shape on the respective chip patterns on the regions A and B are always simultaneously illuminated while the regions A and B on the next reticle are scanned.

If the angle between the light beams $B_1$ and $B_2$ when they are emanated from the polygon mirror 106 is represented by $\alpha$ (deg.), and the synthesized focal length of the lenses 107 and 108 is represented by f, the following expression holds:

$$J = f \times (\pi/180) \times \alpha.$$

FIG. 8 is a block diagram showing another example of the electrical processing system. This example differs from the example shown in FIG. 7 in that a delay circuit 310 is provided after the output unit of the A/D converter 302a. In the present example, an amount which cannot be completely adjusted after the adjustment of the interval J between the points $P_A$ and $P_B$ by the actuator 400 is adjusted by controlling the signal delay time of the delay circuit 310. That is, if scanning of a predetermined portion of the pattern in the region A by the light beam $B_1$ is earlier in time than scanning of the same portion of the pattern in the region B by the light beam $B_2$, the operator delays the arrival time of the signal to the comparator 303 by the amount of the deviation in time by the delay circuit 310. Thus, signals from the positions of the pattern having the same shape in the regions A and B can simultaneously reach the comparator 303. In this case, the adjustment by the actuator 400 is performed so that the light beam $B_1$ does not retard from the light beam $B_2$ in scanning the respective positions of the patterns having the same shape. In the present example, the system may have the configuration such that if there is not much difference in the interval between the regions A and B between the preceding reticle and the next reticle to be inspected, and the interval can be compensated for by adjusting the delay circuit 310 alone. Accordingly, the operator can select to compensate for the interval by using only the delay circuit 310 without performing adjustments using the actuator 400.

In FIGS. 7 and 8, the A/D converters 302a and 302b may be omitted, and analog signals may be compared with each other.

In the present embodiment, in order to perform inspection by comparing plural-chip reticles, simultaneous scanning of a plurality of beams is performed using the same beam scanning optical system, and a mechanism for adjusting the distance between beams on a reticle is provided. Hence, the present embodiment has the following advantages:

1. Since differential processing by a comparison method is performed, no problem will arise even if a small number of light beams diffracted by the patterns are mixed in the respective detectors. This means that light beams can be received in the vicinity of directly reflected light beams where the amount of light scattered by a foreign particle is large. As a result, it is possible to perform detection which is less influenced by disturbance, such as optical flare, electrical noise and like. Accordingly, a finer particle can be detected.

2. In the conventional comparison method using image processing, images in a narrow field of view are connected while repeating stage feeding operations. In the present embodiment, however, since scanning of the entire surface is performed by moving light beams in at least one direction, the time for inspection can be greatly reduced.

3. Since a plurality of light beams perform scanning using the same optical system (comprising a polygonal mirror and a scanning lens), and optical paths of the beams after they pass through the system are substantially the same, it is possible to perform scanning using light beams having the same shape at the same speed. Moreover, it is possible to provide a comparison inspection apparatus with high reliability, since variations of the same degree are produced even if a change during the lapse of time occurs, and therefore outputs for comparison are not influenced.

4. It is possible to perform inspection by easily adjusting the interval between light beams on a reticle even for reticles in which chips are arranged differently.

Figure 9:
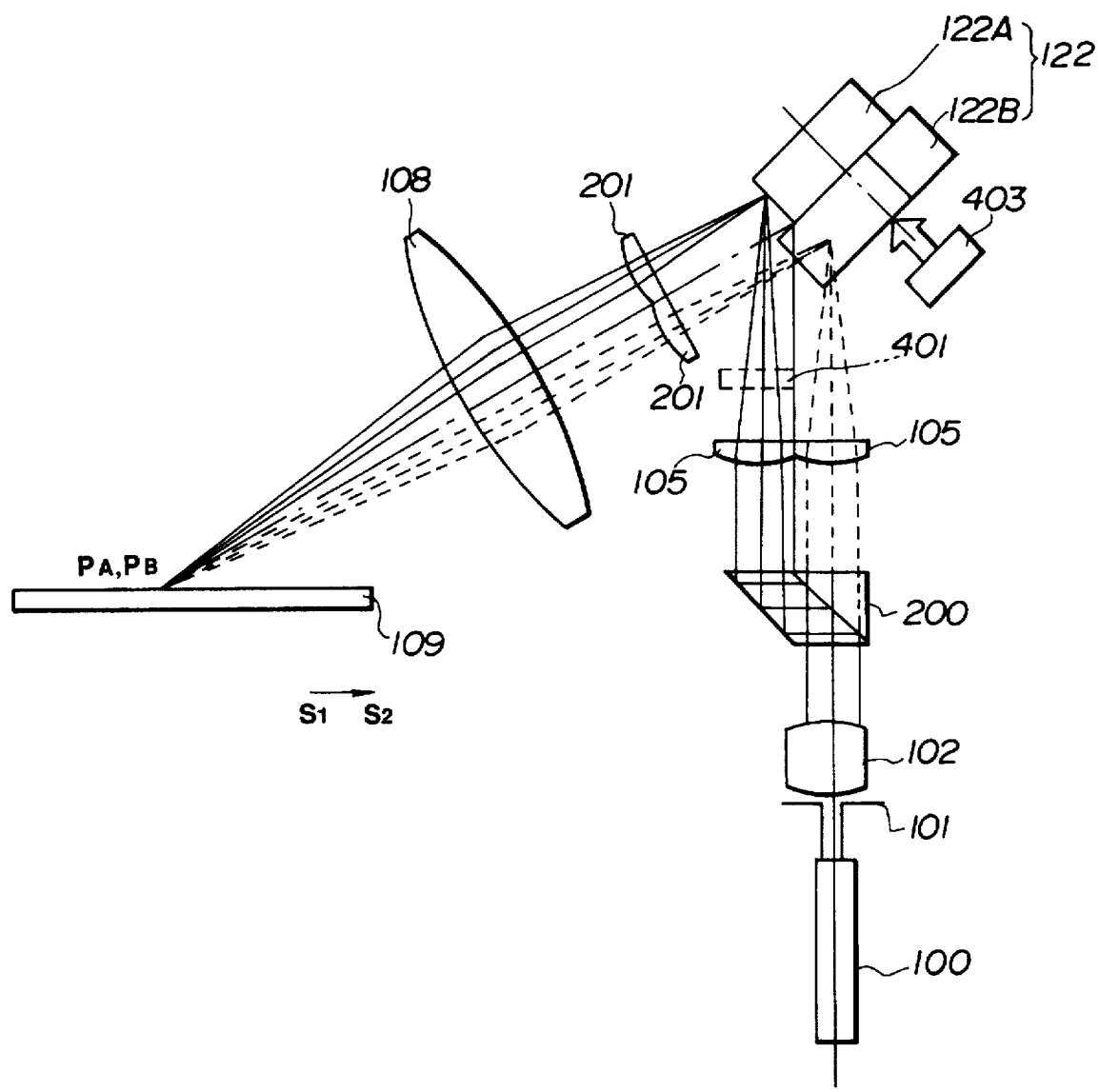
FIG. 9 is a front view showing the schematic configuration of a second embodiment of the present invention.

FIG. 9 is a front view showing the schematic configuration of a second embodiment of the present invention. In FIG. 9, the same components as those shown in FIG. 1 are indicated by the same reference numerals.

In the first embodiment, in order to provide a distance between points irradiated by two light beams on a reticle, two light beams having a separation angle $\alpha$ (deg.) therebetween are incident upon the polygon mirror 106. In the present embodiment, by integrating two polygonal mirrors 122A and 122B as one body while shifting them in the direction of rotation, two light beams having a predetermined interval between irradiated points on the reticle are provided.

Figure 10A:
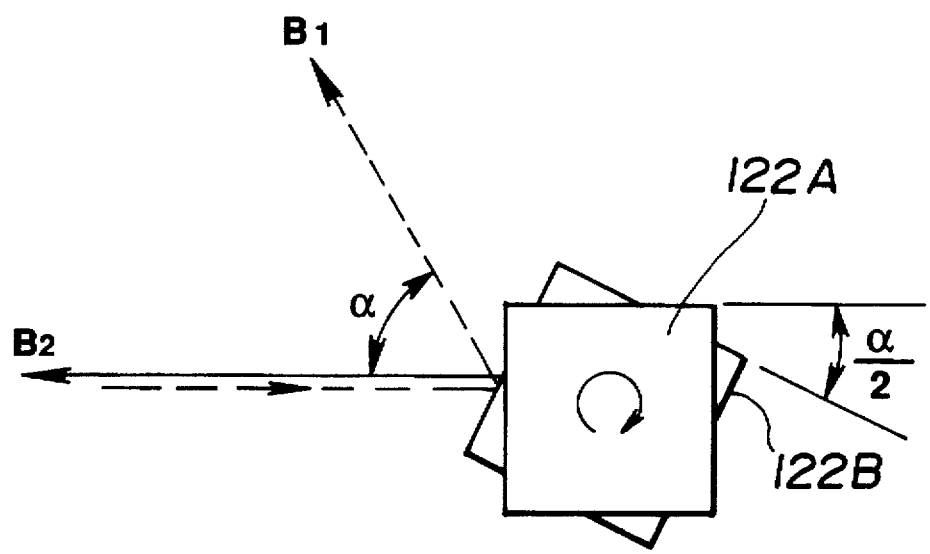
FIGS. 10A and 10B are diagrams illustrating a polygon-mirror unit.
Figure 10B:
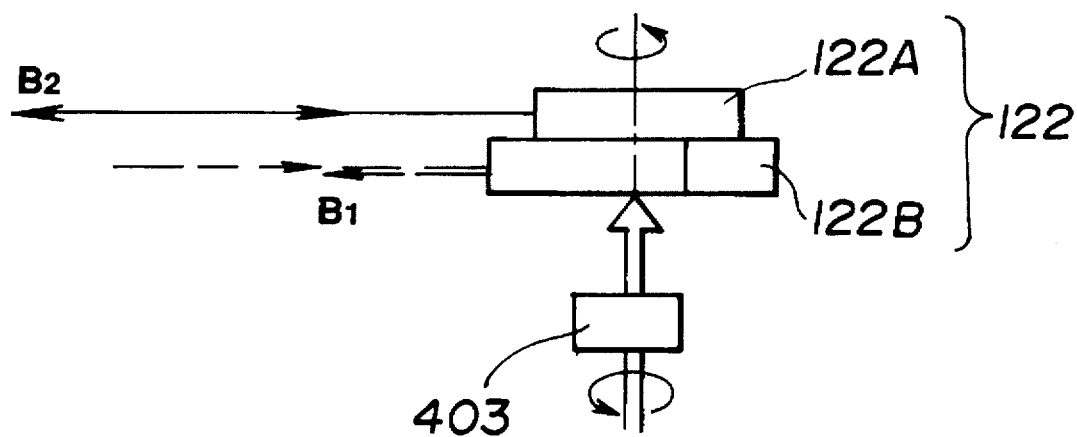

First, the function of a polygon-mirror unit 122 will be explained with reference to FIG. 10A and FIG. 10B. FIG. 10A is a view (a top plan view) of the unit within its plane of rotation. As can be understood from FIG. 10A and FIG. 10B, the polygon-mirror unit 122 is formed by integrating into one body two tetrahedral polygonal mirrors having the same shape while shifting them by an angle $\alpha/2$ (deg.) in the direction of rotation. If light beams $B_1$ and $B_2$ are incident from the same direction, then while the light beam $B_2$ incident upon the upper polygon mirror 122A is reflected in the incident direction, the light beam $B_1$ incident upon the lower polygon mirror 122B is reflected in the direction of an angle $\alpha$ (deg.). FIG. 10B is a view (a front view) of the unit within a plane orthogonal to the plane of rotation.

Referring again to FIG. 9, the light beam passing through the beam expander 102 is incident upon a prism 200 for branching the optical path. The laser light beams divided by the prism 200 are incident upon respective cylindrical lenses 105 having the same function as the cylindrical lens 105 shown in FIG. 1. The optical axes of the respective cylindrical lenses 105 are parallel to each other, and are also parallel to the optical axis of the beam expander 102.

The two light beams passing through the two cylindrical lenses 105 are focused onto the respective polygonal mirrors of the polygon-mirror unit 122, and are again made to be divergent light beams. The respective light beams are converged by the function of two toric lenses 201 and the scanning lens 108, and form respective focused light beams on points $P_A$ and $P_B$ on the reticle. In this configuration, if the shifted angle between the polygonal mirrors 122A and 122B is made to be $\alpha/2$ (deg.) as described above, the synthesized focal length of the toric lenses 201 and the scanning lens 108 is represented by f, and the interval between the positions $P_A$ and $P_B$ irradiated by the two light beams is represented by J, the following expression holds:

$$f \times (\pi/180) \times \alpha = J \qquad (1).$$

It is assumed that the beam scanning system has an f-θ characteristic. In such a case, beam scanning is performed while exactly maintaining the interval between the two points on the reticle at a constant value (J). If the distortion characteristic of the beam scanning system deviates from the f-θ characteristic, it is estimated that the points irradiated by the two light beams deviate from the same pattern positions on the same chip pattern regions during beam scanning. In such a case, an electrical correction may be performed using previously measured characteristics of the lenses. The correction is performed, for example, by changing the signal delay time of the delay circuit shown in FIG. 8 in accordance with characteristics of the lenses.

Another feature of the present embodiment resides in providing the toric lenses 201 to be eccentric and parallel with respect to the optical axis of the scanning lens 108. By providing such an arrangement, the focused points $P_A$ and $P_B$ of the light beams on the reticle exactly coincide with each other without deviating in the moving direction of the reticle ($S_1 \rightarrow S_2$ in FIG. 9, while separated by the interval J in a direction orthogonal to the plane of FIG. 9). This fact will be explained with reference to FIG. 11.

Figure 11:
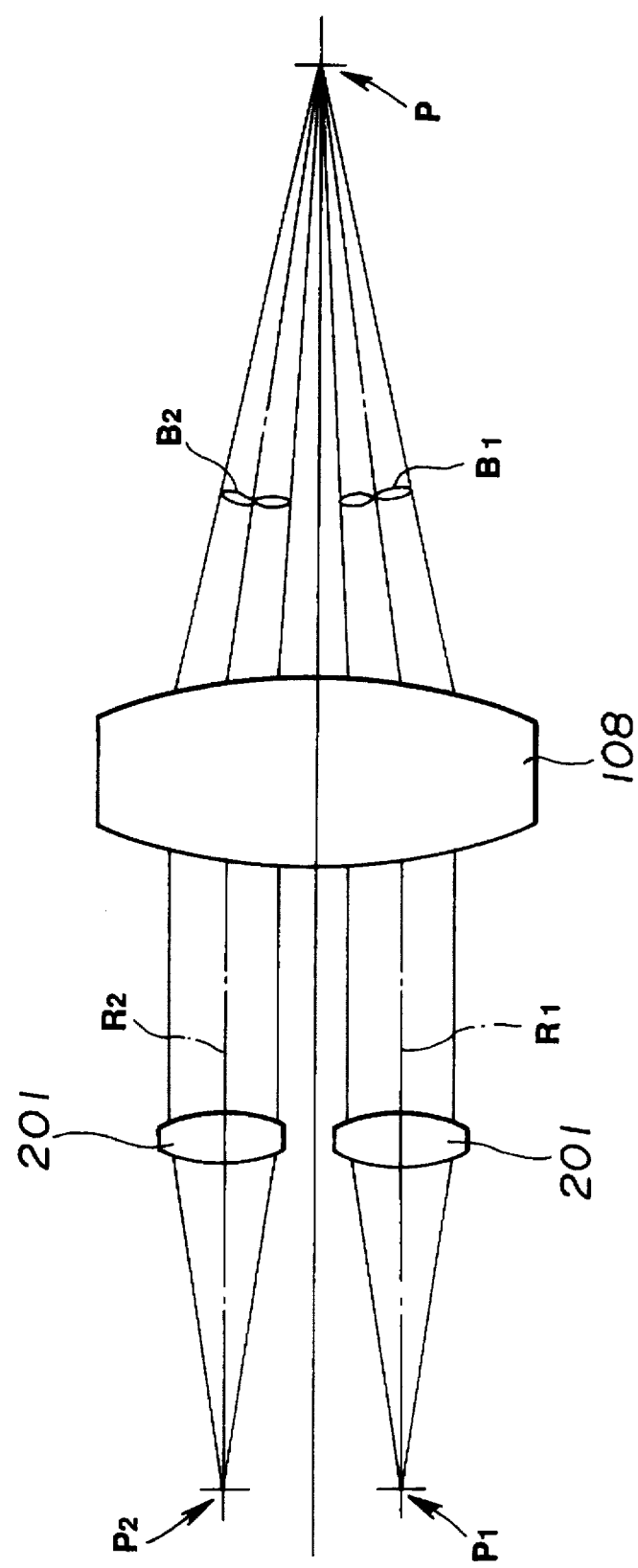
FIG. 11 is a diagram illustrating a scanning optical system.

FIG. 11 depicts the optical paths after the light beams are reflected from the polygon-mirror unit 122 until the light beams are incident upon the reticle.

In FIG. 11, points $P_1$ and $P_2$ represent reflected points of the light beams on the polygon mirrors 122B and 122A, respectively. The respective reflected and divergent light beams become convergent light beams after passing through the respective toric lenses 201 and the scanning lens 108. Since the optical axes of the toric lenses 201 are arranged to be eccentric and parallel with respect to the optical axis of the scanning lens 108, so that the central rays (hereinafter termed principal rays, represented by $R_1$ and $R_2$) of the respective light beams pass through the optical axes of the respective toric lenses 201, the principal rays $R_1$ and $R_2$ are incident upon the scanning lens 108 in parallel without being influenced by the refracting function of the toric lenses 201 within the plane shown in FIG. 11. The amounts of eccentricity of the respective toric lenses 201 are not necessarily the same. In general, light beams incident upon a lens in parallel are focused onto one point (within a permissible range of aberration). Hence, also in this case, each of the principal rays $R_1$ and $R_2$ is exactly focused onto one point (indicated by P in FIG. 11) within the plane of FIG. 11. In addition, since the system is designed so that light beams surrounding the respective principal rays are subjected to the same converging function using the scanning lens 108 as the respective pricipal rays they are naturally focused onto the same position along the principal rays after passing through the scanning lens 108.

From the above-described characteristics, by providing the optical arrangement shown in FIG. 9, alignment of the two beams in the moving direction of the reticle is in principle unnecessary.

Also in the present embodiment, if alignment in the moving direction of the reticle is performed, a single toric lens (or cylindrical lens) may be used along the optical axis of the scanning lens 108, as in the first embodiment. In the present embodiment, the interval J between the points $P_A$ and $P_B$ irradiated by the two light beams shown in FIG. 1 is adjusted in the following way. That is, in FIG. 9, by inserting an optical wedge (or light-beam deflection means, such as a prism) 401 in the optical path of one of the two light beams incident on the polygon-mirror unit 122, the incident angle and the incident position of the light beam on the polygonal mirror 122A are changed. The value J is thereby greatly changed. By changing the amount of insertion of the optical wedge 401, the incident position on the polygon mirror 122A is changed. It is thereby possible to finely adjust the value J.

Alternatively, by providing an actuator 403 for changing the shift angle α/2 between the two polygon mirrors 122A and 122B of the polygon-mirror unit 122, and changing the shift angle using the actuator 403, it is possible to adjust the value J according to expression (1).

Since the light-receiving optical system and the electrical processing system of the present embodiment are the same as in the first embodiment, an explanation thereof will be omitted.

In the above-described embodiments, an explanation has been provided of the configuration of apparatuses when reticles having two-chip arrangement are used. In general, however, the present invention may be applied to a reticle in which an arbitrary number of chips are arranged. For example, when inspecting a reticle having a three-chip arrangement, light beams may be incident upon the polygonal mirror 106 from three directions in the embodiment shown in FIG. 1. In the embodiment shown in FIG. 9, a three-staged polygon-mirror unit may be used. In both embodiments, the light-receiving system shown in FIG. 4 may be modified such that the optical path after the field stop is divided into three paths, and three light beams are sensed by three photoelectric devices to be subjected to comparison processing.

Figure 12:
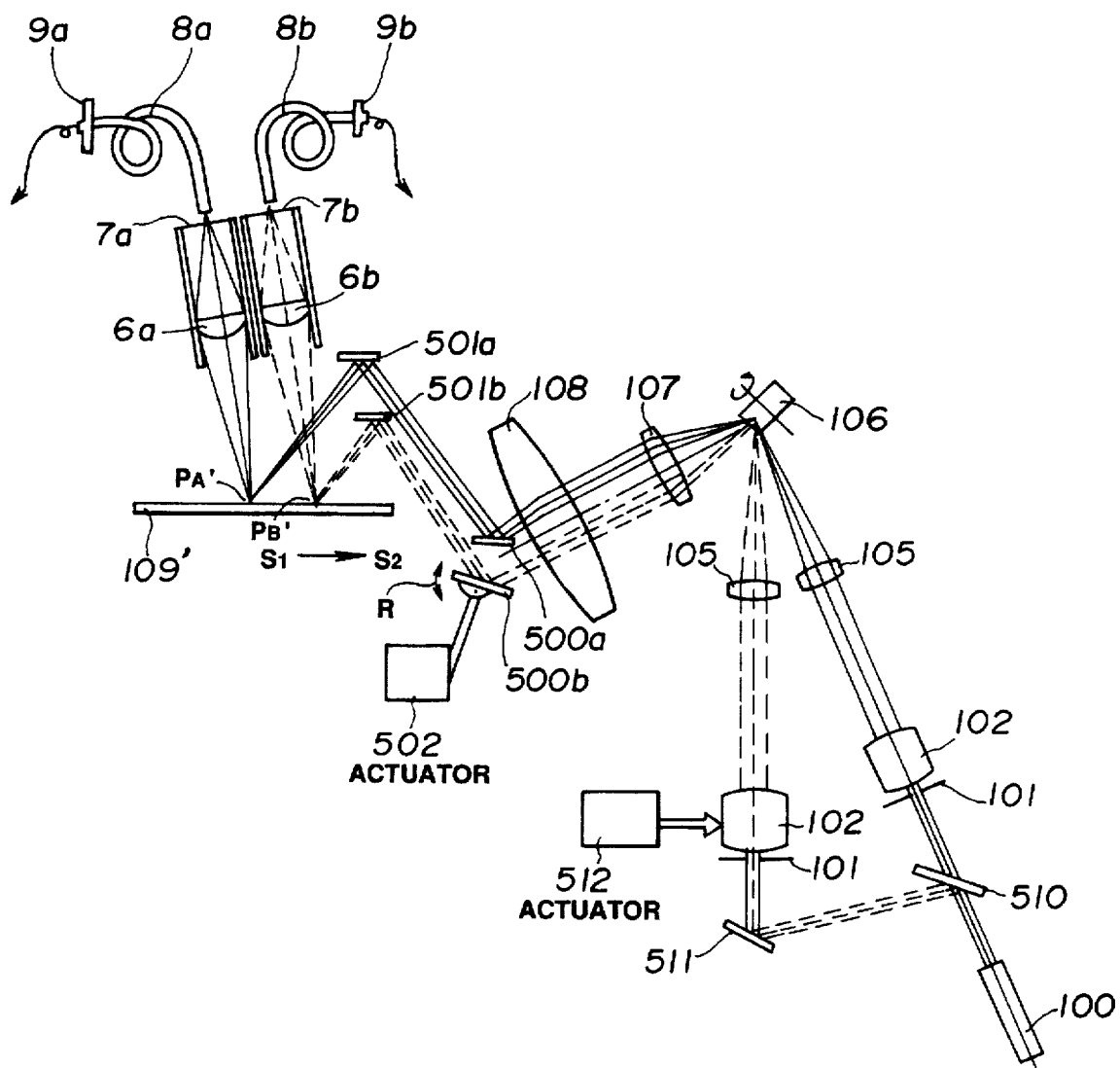
FIG. 12 is a front view showing the schematic configuration of a third embodiment of the present invention.
Figure 15:
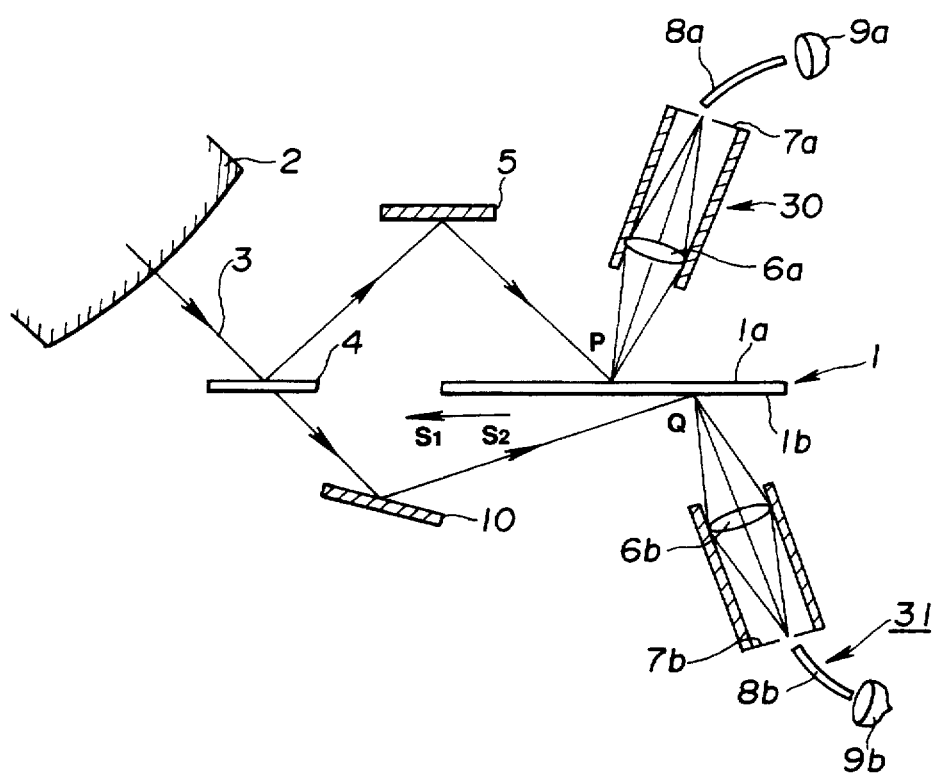
FIG. 15 is a diagram illustrating a conventional inspection apparatus.

FIG. 12 is a front view showing the schematic configuration of a third embodiment of the present invention. In FIG. 12, the same components as those shown in the above-described embodiments are indicated by the same reference numerals. An explanation will be provided of items different from the apparatus shown in FIG. 2. A light beam emitted from the laser 100 is divided into two beams by a half-mirror 510. The reflected light beam is further reflected by a mirror 511, passes through the pinhole 101 and the beam expander 102, and is incident upon the polygonal mirror 106 via the cylindrical lens 105 from a direction different from that of the directly advancing light beam. The two light beams pass outside the optical axes of the toric lens 107 and the scanning lens 108, are reflected by mirrors 500a and 500b, and 501a and 501b, respectively, and are focused onto two points $P'_A$ and $P'_B$ separated by a distance R in the moving direction of the reticle ($S_1 \rightarrow S_2$) on the reticle 109' while being scanned. Scattered light beams or O-order reflected light beams (or transmitted light beams) from the respective points are received by light-receiving systems (light-receiving lenses 6a and 6b, field stops 7a and 7b, fibers 8a and 8b, and photomultipliers 9a and 9b) shown in FIG. 15. The outputs of the photomultipliers 9a and 9b are subjected to electrical processing shown in FIG. 7 as detector outputs.

In the above-described configuration, the two light beams incident upon the polygon mirror 106 also have different incident angles in a direction perpendicular to the plane of FIG. 12 by the function of the half-mirror 510 and the mirror 511, and, as in the case of FIG. 1, points irradiated by the two light beams are separated by a predetermined distance (J) in the scanning direction of the light beams (a direction perpendicular to the plane of FIG. 12). In FIG. 12, there is shown an actuator 502 for rotating the mirror 500b in the directions of the two-headed arrow R. By the function of the actuator 502, the point $P_B$ moves in the direction $S_1 \rightarrow S_2$ and in the opposite direction, whereby the value R can be changed. At that time, however, the optical path length changes, and therefore the light beam is not focused onto the point $P_B$. In order to compensate this change, the system is configured so that the refractive power (that is, the focal length) of the beam expander 102 is changed by an actuator 512.

Figure 13:
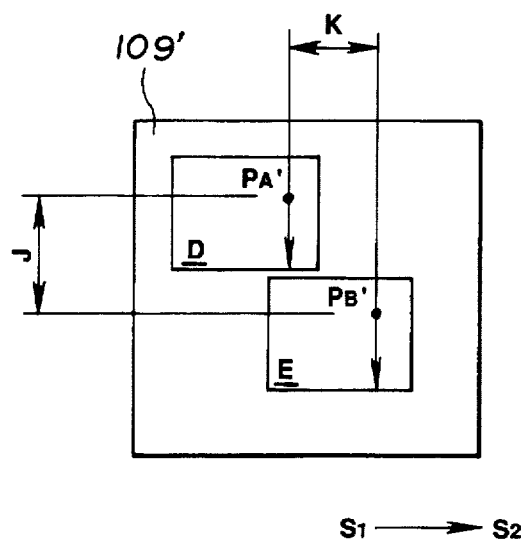
FIG. 13 is a diagram illustrating an arrangement of chip patterns.

FIG. 13 is a top plan view of a reticle 109' illustrating setting of the light beams in the configuration of the present invention when chips D and E are arbitrarily arranged on the reticle 109'. As described above, the two light beams are focused onto points P'$_A$ and P'$_B$ separated by a distance J in the scanning direction of the light beams and a distance K in the moving direction of the reticle, and scanning is performed in the direction of respective arrows.

Figure 16:
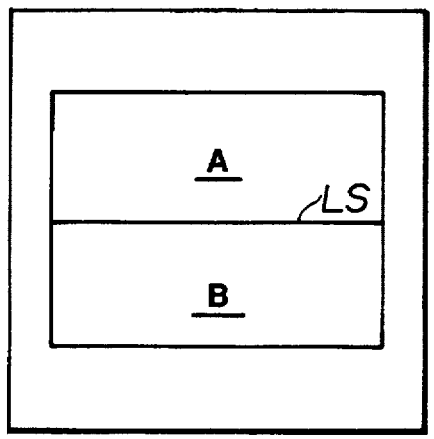
FIGS. 16(a) through 16(c) are diagrams illustrating alternative arrangements of chip patterns.
Figure 16:
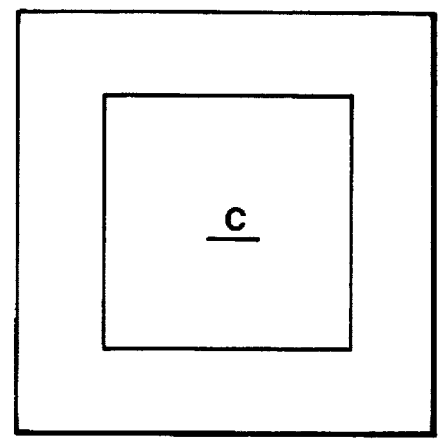
Figure 16:
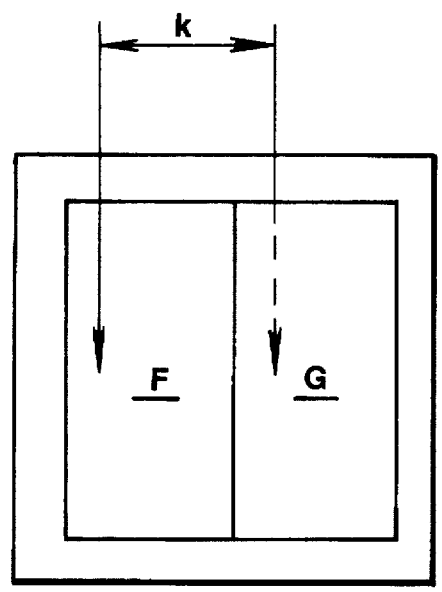
Figure 17:
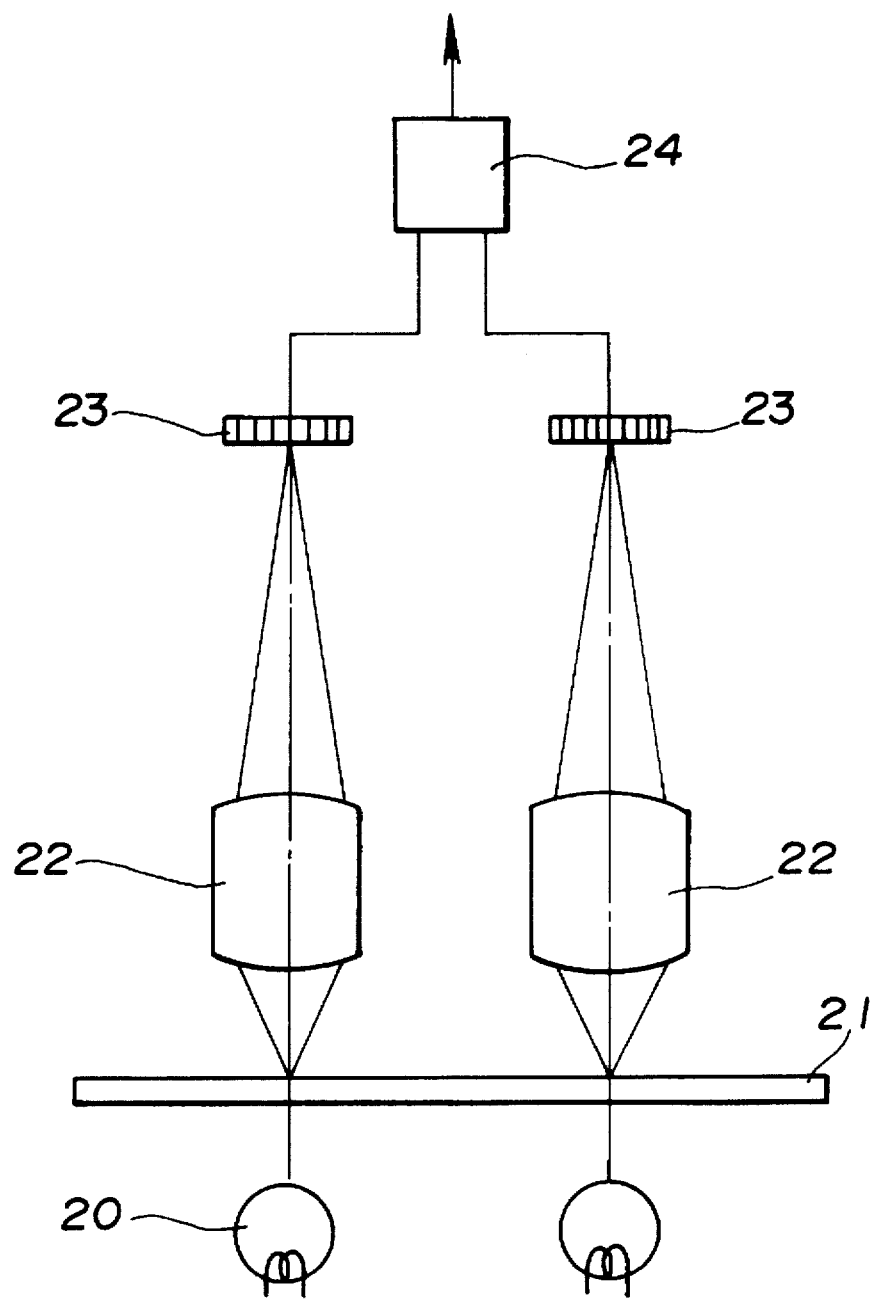
FIG. 17 is a diagram illustrating another conventional inspection apparatus.

In FIG. 13, if J=0, the chip arrangement shown in FIG. 16(c) can be inspected.

The means for adjusting the interval between the points P'$_A$ and P'$_B$ in the direction S$_1$→S$_2$ shown in FIG. 12 may, of course, be applied to the embodiment which uses the polygon-mirror unit 122 shown in FIG. 9. In this case, it is unnecessary to provide a difference in the incident angles of the two light beams incident upon the polygon mirror in the direction perpendicular to the plane of FIG. 12.

Although the actuator 502 is provided for the mirror 500b in the case of FIG. 12, the actuator 502 may be provided for any or a plurality of the other mirrors 500a, 501a and 501b. The actuator 502 may not only rotatably drive the mirror, but also translationally drive the mirror.

Although an explanation has been provided of comparative inspection of the pattern surface of a reticle on which a plurality of chip patterns are formed, the present invention is not limited to such a case.

That is, the present invention may be applied to foreign-particle inspection on the blank surface not subjected to patterning in the same manner as in the case of inspection of the pattern surface, provided that a plurality of chip patterns are present on the pattern surface at the back side. That is, scanning so that respective portions at the back side corresponding to the positions having the same shape on the patterns are simultaneously irradiated by the light beams may be performed in the same manner as described above. The present invention may also be applied to surface-condition inspection of a substrate provided with a dustproof pellicle.

The present invention may be applied not only to foreign-particle inspection, but also to pattern-defect inspection.

In the configuration of the present invention, a CCD (charge-coupled device) array sensor or a multisegment sensor may be used at the position of the field stop 113 (or 7a and 7b), and outputs of corresponding picture elements may be directly compared.

The present invention may also be applied to an optical arrangement in which a vibrating mirror is used in place of the polygon mirror, and correction for inclination is not performed.

Although an explanation has been provided of the case of using reflected light beams as light beams to be received, light beams transmitted through the reticle (or transmitted scattered light beams) may be received and compared with each other. The incident angle of the beam is not limited to an oblique angle relative to the reticle, but vertically-incident light beams may also be used.

Figure 14:
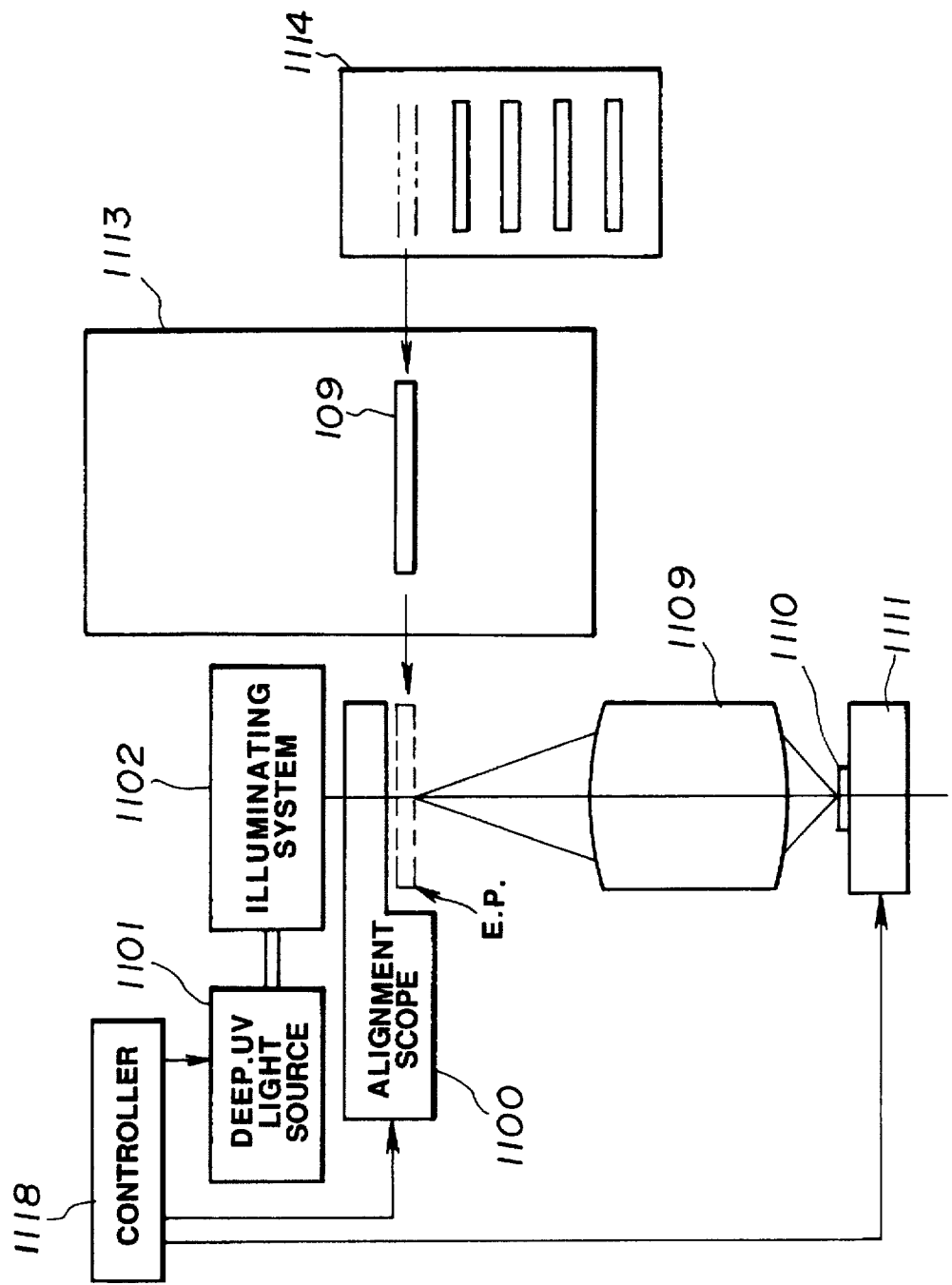
FIG. 14 is a diagram showing the schematic configuration of an exposure apparatus using the present invention.

FIG. 14 is a diagram showing the configuration of a surface-condition inspection apparatus according to still another embodiment of the present invention. In the present embodiment, the entire inspection apparatus is incorporated within a semiconductor printing apparatus.

In FIG. 14, there is shown a deep-UV light source 1101, such as an excimer laser. An illuminating system 1102 uniformly and simultaneously (at a time) illuminates the entire region to be inspected of the reticle 109 with a predetermined NA (numerical aperture) from above.

An ultrahigh-resolution lens system (or mirror system) 1109 transfers the reticle pattern onto a wafer 1110. In a printing operation, the wafer 1110 is exposed while being shifted shot by shot in accordance with stepping feed of a moving stage 1111. An alignment optical system 1100 aligns the reticle with the wafer before exposure, and includes at least one microscope system for observing the reticle.

A reticle changer 1114 stores a plurality of reticles in a waiting state. A unit 1113 for inspecting foreign particles or the like includes all the components used in the first, second or third preferred embodiment. The unit 1113 inspects for foreign particles on a reticle after the reticle is drawn from the reticle changer 1114 but before it is set at the exposure position (indicated by E. P. in FIG. 14).

A controller 1118 controls the sequence of alignment, exposure and stepping feed of a wafer, which is the basic operation of a stepper.

In the above-described configuration, since the principle and the operation of inspection for foreign particles or the like in the unit 1113 are the same as in any of the above-described embodiments, an explanation thereof will be omitted.

As described above, according to the present invention, it is possible to provide a small-sized apparatus which can perform high-speed and high-precision inspection without being influenced by the state of chip pattern arrangement on a reticle.

The individual components shown in outline or designated by blocks in the drawings are all well-known in the surface condition inspection apparatus arts and their specific construction and operation are not critical to the operation or best mode for carrying out the invention.

While the present invention has been described with respect to what is presently considered to be the preferred embodiments, it is to be understood that the invention is not limited to the disclosed embodiments. To the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. An apparatus for inspecting a surface of an object, said apparatus comprising:

generating means, comprising a light source, for generating first and second beams different from each other;

scanning means comprising a scanning optical system including a common scanning mirror and at least one common focusing element disposed in an optical path after the scanning mirror, for scanning each of the first and second beams onto first and second areas of the surface of the object;

adjusting means, provided at least in an optical path of the second beam between said light source and said scanning mirror, for adjusting an interval of the scanning beams on the surface of the object; and means for independently detecting the beams from the respective first and second areas to inspect the surface of the object.

2. An apparatus according to claim 1, wherein the object is a reticle having first and second patterns corresponding to the first and second areas.

3. An apparatus according to claim 2, wherein said common focusing optical element comprises a scanning lens.

4. An apparatus according to claim 1, wherein said light source comprises a laser source.

5. An apparatus according to claim 4, wherein said common focusing optical element comprises a scanning lens.

6. An apparatus according to claim 1, further comprising exposure means for exposing the inspected object with exposure beams.

7. An apparatus according to claim 6, wherein said common focusing optical element comprises a scanning lens.

8. An apparatus according to claim 1, wherein said common focusing optical element comprises a scanning lens.

9. An apparatus for scanning a surface of an object, said apparatus comprising:

generating means, comprising a light source, for generating first and second beams different from each other;

common scanning means comprising a scanning optical system including a scanning mirror and at least one common focusing optical element disposed in an optical path after the scanning mirror, for scanning each of the first and second beams onto first and second areas of the surface of the object; and adjusting means, provided at least in an optical path of the second beam between said light source and said scanning mirror, for adjusting an interval of the scanning beams on the surface of the object.

10. An apparatus according to claim 9, wherein said common focusing optical element comprises a scanning lens.

* * * * *

UNITED STATES PATENT AND TRADEMARK OFFICE
CERTIFICATE OF CORRECTION

PATENT NO. : 5,528,360
DATED : June 18, 1996
INVENTOR(S) : Michio KOHNO

It is certified that error appears in the above-indentified patent and that said Letters Patent is hereby corrected as shown below:

COLUMN 1:

Line 42, "f-8 lens" should read --f-θ lens--; and
    Line 51, "inspecting" should read --inspecting for--.

COLUMN 5:

Line 38, "condensor" should read --condenser--; and
    Line 41, "FIG. 8," should read --FIG. 5,--.

COLUMN 6:

Line 6, "FIGS. 6(a" should read --FIGS. 6(a)--.

Signed and Sealed this

Tenth Day of December, 1996

*Attest:*

BRUCE LEHMAN

*Attesting Officer*    *Commissioner of Patents and Trademarks*